United States Patent
Ludin

(10) Patent No.: US 7,226,430 B2
(45) Date of Patent: Jun. 5, 2007

(54) CLOSED LOOP SYSTEM AND METHOD FOR CONTROLLING MUSCLE ACTIVITY VIA AN INTRATHECAL CATHETER

(75) Inventor: Lev Ludin, Newton, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 180 days.

(21) Appl. No.: 10/745,715

(22) Filed: Dec. 26, 2003

(65) Prior Publication Data

US 2005/0148927 A1    Jul. 7, 2005

(51) Int. Cl.
*A61M 31/00* (2006.01)
(52) U.S. Cl. ...................................... 604/67
(58) Field of Classification Search ............... 604/67, 604/66, 65; 128/DIG. 12, 13; 600/300–301; 607/29–32, 60
See application file for complete search history.

(56) References Cited

U.S. PATENT DOCUMENTS

| | | | |
|---|---|---|---|
| 4,280,494 A | 7/1981 | Cosgrove, Jr. et al. | 128/213 R |
| 4,392,849 A | 7/1983 | Petre et al. | 604/66 |
| 4,570,640 A * | 2/1986 | Barsa | 600/554 |
| 4,979,940 A | 12/1990 | Bobo, Jr. et al. | 604/50 |
| 5,423,877 A | 6/1995 | Mackey et al. | |
| 5,711,316 A * | 1/1998 | Elsberry et al. | 128/898 |
| 5,735,814 A | 4/1998 | Elsberry et al. | 604/43 |
| 5,978,702 A | 11/1999 | Ward et al. | 607/3 |
| 6,042,579 A | 3/2000 | Elsberry et al. | 604/891.1 |
| 6,263,237 B1 | 7/2001 | Rise | 607/3 |
| 6,471,645 B1 * | 10/2002 | Warkentin et al. | 600/300 |
| 6,862,479 B1 * | 3/2005 | Whitehurst et al. | 607/39 |
| 2002/0042590 A1 | 4/2002 | Hubbard, Jr. | |
| 2002/0087114 A1 | 7/2002 | Hartlaub | |

* cited by examiner

Primary Examiner—Manuel Mendez
(74) Attorney, Agent, or Firm—Cheryl F. Cohen, LLC

(57) ABSTRACT

A closed loop feedback drug delivery system for controlling muscle activity, e.g., spasticity. The system includes a sensor, e.g., an EMG sensor, for monitoring muscle activity and generating a detected muscle activity signal. A controller automatically adjusts at least one of timing and dosage of a drug administered to control muscle activity based on the detected muscle activity signal and produces a control signal. Administering of the drug, e.g., an antispasmodic drug, for controlling muscle activity based on the control signal is performed by an infusion pump. The drug after being emitted from the pump is then delivered to the spinal cord of the patient using an intrathecal catheter.

16 Claims, 2 Drawing Sheets

CLOSED LOOP SYSTEM AND METHOD FOR CONTROLLING MUSCLE ACTIVITY VIA AN INTRATHECAL CATHETER

BACKGROUND OF THE INVENTION

1. Field of the Invention

The present invention is directed to a drug delivery system and, in particular, to a closed loop system and method for controlling muscle activity by infusion of drugs, e.g., antispasmodic drugs, via an intrathecal/intraspinal catheter.

2. Description of Related Art

Muscle disorders can have debilitating effects on an individual's daily life. It is desirable to administer drugs to reduce or control undesirable muscle activity. By way of example, spasticity is an abnormal involuntary muscle activity with increased muscle tone (rigidity) and sustained muscle contractions (spasm) caused by damage to the central nervous system resulting, for example, from a spinal cord or head injury. Often spasticity is but a symptom associated with a disorder such as multiple sclerosis, cerebral palsy, stroke, Parkinson's or Epilepsy.

There is a widespread degree of spasticity ranging from moderate to severe. Moderate spasticity may have little interference in the patient's normal life and typically is controlled by physical therapy and/or oral muscle relaxants. Patients that suffer from severe spasticity may be treated by way of intrathecal therapy administering the drug directly to the spinal subarachnoid space via an implantable pump. There are two main types of pumps that can be implanted for administration of drug via the intrathecal catheter. A fixed rate pump may be used to control the drug dosage, but this device does not permit dosage adjustment. Alternatively, a pump may be used that is capable of being programmed by a physician via an external battery powered computer to alter the drug dosage. This, however, is still disadvantageous in that it requires a physician or clinician to adjust or control the drug dosage. It would be desirable to adjust the drug dosage automatically without intervention by a physician or clinician.

Other types of undesirable muscle activity may likewise have a negative impact on one' daily activities and life. U.S. Pat. No. 6,263,237 discloses a method for the treatment of anxiety disorders by brain stimulation and drug infusion. Specifically, closed-loop feedback infusion of medicine and stimulation directly to the brain is disclosed in response to an electromyograph (EMG) sensor signal. The EMG sensor signal detects anxiety disorder related symptoms, e.g., excessive muscle tension or tremors. Since anxiety is controlled by the neural circuitry of the brain, the drug is delivered directly to the brain. This patented method closed-loop feedback infusion of antianxiety drugs directly to the brain based on the detection of muscle activity is disclosed exclusively for the treatment of anxiety disorders.

It is therefore desirable to subside, reduce, eliminate or control muscle activity by developing a closed loop feedback drug delivery system for the infusion of a drug directly to the spinal cord the dosage of which is automatically controlled based on detected muscle activity without intervention by a physician or clinician.

SUMMARY OF THE INVENTION

The present invention is directed to a closed loop feedback drug delivery system for controlling muscle activity. The system in accordance with the invention includes a sensor, e.g., an EMG sensor, for monitoring muscle activity and generating a detected muscle activity signal. A controller automatically adjusts at least one of timing and dosage of a drug administered to control muscle activity based on the detected muscle activity signal and produces a control signal. Administering of the drug, e.g., an antispasmodic drug, for controlling muscle activity based on the control signal is performed by an infusion pump. The drug after being emitted from the pump is then delivered to the spinal cord of the patient using an intrathecal catheter.

In addition, the invention also relates to a method for controlling muscle activity using the closed loop feedback drug delivery system described above. Initially muscle activity is monitored and a detected muscle activity signal is generated by a sensor, e.g., an EMG sensor. The timing and/or dosage of a drug administered to control muscle activity based on the detected muscle activity signal are automatically adjusted and a control signal is produced by a controller. The drug for controlling muscle activity based on the control signal is administered by a pump. Finally, the drug to be administered is delivered via an intrathecal catheter to the spinal cord.

In a first embodiment, the sensor and controller are implanted beneath the skin of the patient and communication between the controller and pump is via a wireline communication. However, it is also contemplated and within the intended scope of the present invention for a surface sensor to be employed whereby communication between the controller and pump is via wireless communication, e.g., a telemetric link and associated antenna.

BRIEF DESCRIPTION OF THE DRAWING

The foregoing and other features of the present invention will be more readily apparent from the following detailed description and drawings of illustrative embodiments of the invention wherein like reference numbers refer to similar elements throughout the several views and in which.

DETAILED DESCRIPTION OF THE INVENTION

Figure 1:
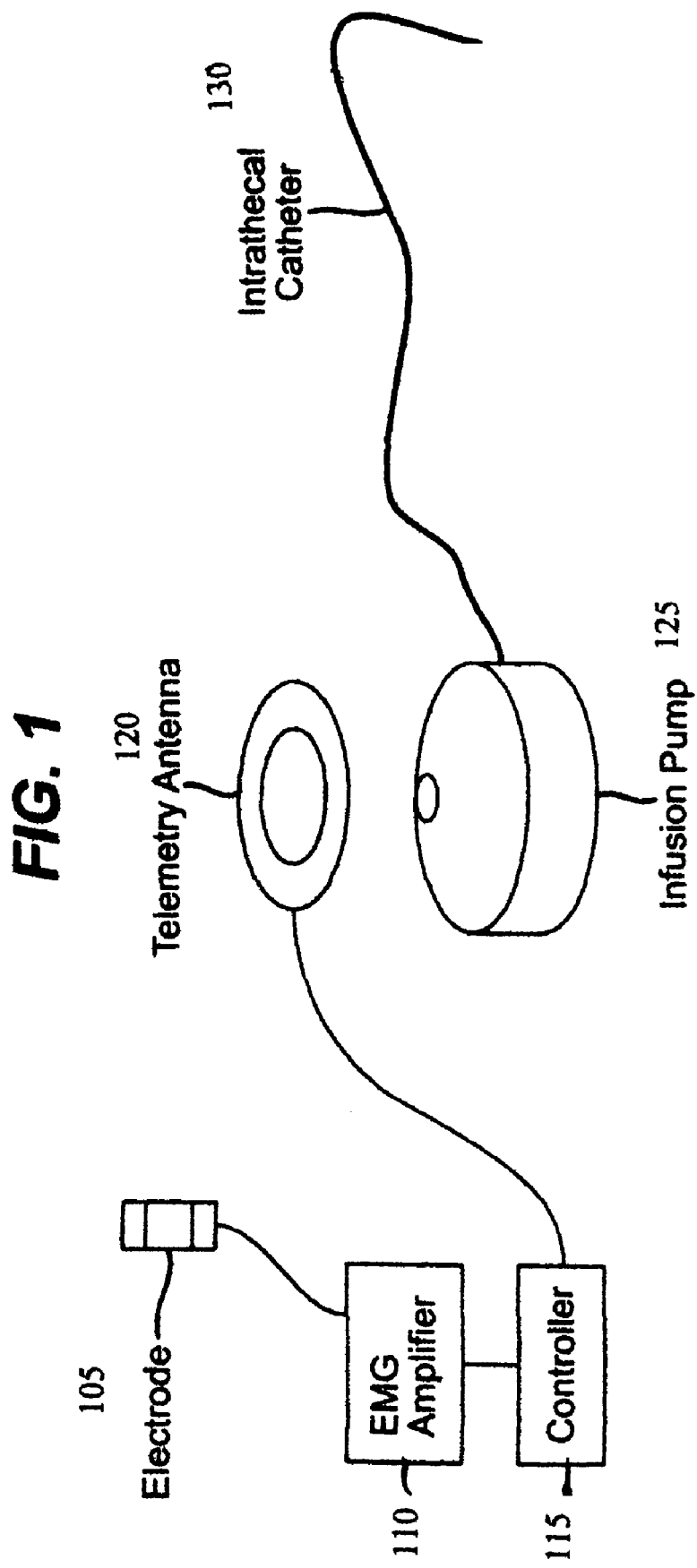
FIG. 1 is an exemplary schematic diagram of a first embodiment of a closed loop feedback drug delivery system for controlling muscle activity in accordance with the present invention.

An exemplary schematic circuit diagram of a first embodiment of a closed loop feedback drug delivery system 100 for controlling spasticity in accordance with the present invention is shown in FIG. 1. An EMG sensor 105 or any other type of sensor used to monitor muscle activity may be employed. In the example shown in FIG. 1, an EMG sensor 105 is disposed externally proximate a muscle of the patient's body (e.g., hand, arm, foot, leg, facial muscle, back muscle) that is prone to spasticity. The EMG sensor measures the electrical activity in a muscle, and is monitored by a surface electrode placed externally on the skin positioned proximate a muscle to be monitored or by a needle electrode inserted directly into muscle fibers. Any type of EMG sensor may be used such as a single surface electrode, a surface electrode array, a needle electrode, or a needle electrode array implanted or inserted into the muscle being monitored. In the case in which an implanted electrode or array is employed, a cable/wire may extend to the skin surface for connection to external circuitry, e.g., an amplifier. Often it is desirable to monitor muscle activity from multiple sensors. Accordingly, it is contemplated and within the intended scope of the present invention to employ multiple EMG sensors at a single area and/or at different locations. Although not shown in the figures, a preamplifier may be included as part of or separate from the EMG sensor to increase signal-to-noise ratio or quality of the EMG output signal.

All muscle activity, whether voluntary or involuntary, produces muscle contractions that may be monitored or detected using an EMG sensor. Increased EMG activity reflects greater motor unit recruitment or an increase in motor unit firing, whereas decreased EMG suggests fewer or weaker nerve signals have been delivered to the muscle. Involuntary muscle activity may be distinguished over voluntary muscle activity based on the degree of randomness of motor unit firing. That is, involuntary muscle activity may have a lower degree of randomness that may be classified based on its repetitive or periodic nature.

EMG sensor 105 produces a detected muscle activity signal that is preferably amplified by amplifier 110. In turn, a controller 115 produces an appropriate drug dosage signal in response to the amplified EMG. In the embodiment shown in FIG. 1, EMG electrode 105, amplifier 110 and controller 115 are external to the body, accordingly the drug dosage signal generated by the controller 115 is communicated by a wireless communication system, e.g., telemetry via antenna 120, to an implanted infusion pump 125. Inherently, implanted infusion pump includes conventional receiver circuitry (not shown). Infusion pump 125 delivers or pumps the proper drug dosage based on the drug dosage signal produced by the controller 115. Typically, the infusion pump 125 is implanted under the skin of the patient's abdomen. The drug to be administered may be morphine, Baclofen or any other drug used to subside, reduce or control muscle activity. An intrathecal catheter 130 is attached to the infusion pump 125 for delivery of the medication in the amount or level specified by the drug dosage signal directly to the spinal cord. Based on the output signal from the EMG sensor 105, the controller 115 produces a drug dosage signal to adjust one or more of the following parameters: periodicity/frequency, duration and/or dosage level.

In operation, when muscle activity is detected by the EMG electrode 105 the amplified EMG signal is received at the controller 115. The timing and/or dosage of drugs delivered via the intrathecal catheter 130 by the implantable pump 125 is set by the controller 115 based on the EMG signal. Accordingly, the delivery of medication to the spinal cord to reduce or eliminate undesirable muscle activity is automatically controlled via software stored in the controller 115 without intervention by a physician or clinician. The software parameters for control of timing and dosage of the medication may be initially programmed by the physician or clinician specifically for that particular patient. Thereafter, monitoring of overall system performance and any adjustments to the parameters may be made by the physician or clinician during periodic checkup or follow-up visits.

Figure 2:
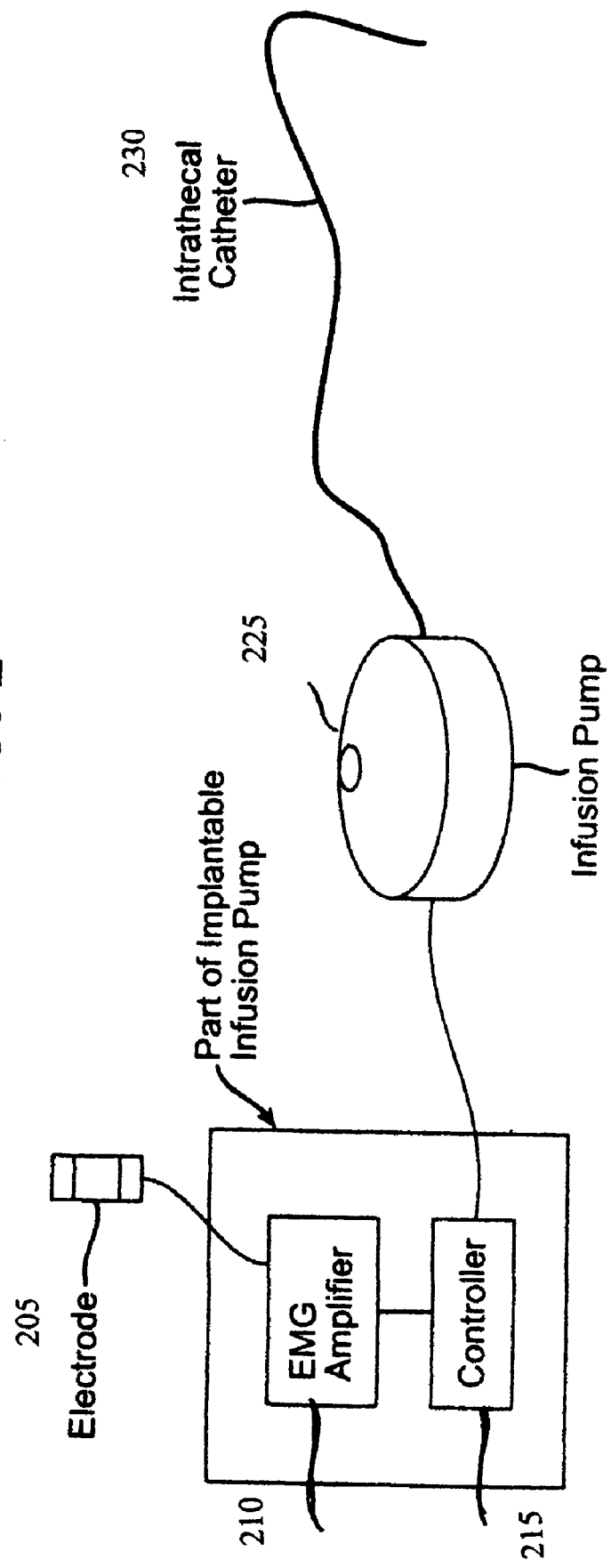
FIG. 2 is an exemplary schematic diagram of a second embodiment of a closed loop feedback drug delivery system for controlling muscle activity in accordance with the present invention.

An alternative embodiment of the present inventive feedback closed loop system is shown in FIG. 2. This second embodiment differs from that of the first embodiment shown in FIG. 1 in that the entire device, including the electrode 205, is part of the implantable drug delivery system. That is the electrode 205 is implanted rather than being disposed externally. Accordingly, the signal is communicated to the implantable pump 225 via an electrical wire/cable instead of a telemetry link. In all other respects the operation of the two embodiments are the same and need not be described further.

Thus, while there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps that perform substantially the same function, in substantially the same way, to achieve the same results be within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

Every issued patent, pending patent application, publication, journal article, book or any other reference cited herein is each incorporated by reference in their entirety.

What is claimed is:

1. A closed loop feedback drug delivery system for controlling muscle activity comprising:
    a sensor for monitoring abnormal muscle activity and generating a detected muscle activity signal;
    a controller for automatically adjusting at least one of timing and dosage of a drug administered to control muscle activity based on the detected muscle activity signal and producing a control signal;
    a pump for administering the drug for controlling muscle activity based on the control signal; and
    an intrathecal catheter delivering the drug dispensed from said pump to the spinal column.

2. The system in accordance with claim 1, wherein the muscle activity is involuntary.

3. The system in accordance with claim 2, wherein the muscle activity is spasticity.

4. The system in accordance with claim 1, wherein the sensor is an EMG sensor in the form of one of a single surface electrode, a surface electrode array, a needle electrode, or a needle electrode array.

5. The system in accordance with claim 1, wherein said controller is wired to said pump.

6. The system in accordance with claim 1, wherein said controller communicates with said pump via wireless communication.

7. The system in accordance with claim 6, wherein the wireless communication is via a telemetric link.

8. A method for controlling muscle activity using a closed loop feedback drug delivery system, comprising the steps of:
    monitoring abnormal muscle activity and generating a detected muscle activity signal;
    automatically adjusting at least one of timing and dosage of a drug administered to control muscle activity based on the detected muscle activity signal and producing a control signal;
    administering a drug for controlling muscle activity based on the control signal; and
    delivering the drug to be administered via an intrathecal catheter to the spinal column.

9. The method in accordance with claim 8, wherein said monitoring step comprises positioning externally a sensor proximate a muscle to be monitored.

10. The method in accordance with claim 9, wherein the sensor is disposed to monitor muscle activity in at least one of a hand, arm, foot, leg, facial muscle, or back muscle.

11. The method in accordance with claim 8, wherein said muscle activity is spasticity.

12. The method in accordance with claim 8, wherein said muscle activity is monitored using an EMG sensor in the form of one of a single surface electrode, a surface electrode array, a needle electrode, or a needle electrode array.

13. The method in accordance with claim 8, wherein said adjusting step comprises receiving the detected muscle activity signal via wireless communications.

14. The method in accordance with claim 13, wherein the wireless communication is via a telemetric link.

15. A method for controlling muscle activity using a closed loop feedback drug delivery system, comprising the steps of:

monitoring naturally occurring muscle activity and generating a detected muscle activity signal;

automatically adjusting at least one of timing and dosage of a drug administered to control muscle activity based on the detected muscle activity signal and producing a control signal;

administering a drug for controlling muscle activity based on the control signal; and delivering the drug to be administered via an intrathecal catheter to the spinal column.

16. A closed loop feedback drug delivery system for controlling muscle activity comprising:

a sensor for monitoring naturally occurring muscle activity and generating a detected muscle activity signal;

a controller for automatically adjusting at least one of timing and dosage of a drug administered to control muscle activity based on the detected muscle activity signal and producing a control signal;

a pump for administering the drug for controlling muscle activity based on the control signal; and an intrathecal catheter delivering the drug dispensed from said pump to the spinal column.

* * * * *